United States Patent [19]

Lowe, III

[11] Patent Number: 4,730,056
[45] Date of Patent: Mar. 8, 1988

[54] PROCESS FOR (1H)-ISOINDOLIN-1-ONE-3-CARBOXYLIC ACID

[75] Inventor: John A. Lowe, III, Stonington, Conn.

[73] Assignee: Pfizer Inc., New York, N.Y.

[21] Appl. No.: 902,344

[22] Filed: Aug. 29, 1986

[51] Int. Cl.[4] ............................................ C07D 209/46
[52] U.S. Cl. ...................................................... 548/472
[58] Field of Search ......................................... 548/472

[56] References Cited
FOREIGN PATENT DOCUMENTS
58567 8/1982 European Pat. Off. .

OTHER PUBLICATIONS

L. Kametani et al., Chem. Abstracts, vol. 69, No. 106401w (1968).
L. Kametani et al, Chem. Abstracts, vol. 71, No. 30191w (1969).
J. Prakt. Chem., vol. 146, 307 (1936).

Primary Examiner—Mary E. Ceperley
Attorney, Agent, or Firm—Peter C. Richardson; Albert E. Frost; James M. McManus

[57] ABSTRACT

A process for preparing [1H]-isoindolin-1-one-3-carboxylic acid comprising the steps of (1) reacting phthalaldehydic acid in an alkanol with ammonia, (2) contacting the resulting solution with an alkali metal cyanide, (3) removing the alkanol, (4) adjusting the pH to 1.0, (5) heating the resulting reaction mixture until product formation is substantially complete and isolating the product.

2 Claims, No Drawings

PROCESS FOR (1H)-ISOINDOLIN-1-ONE-3-CARBOXYLIC ACID

BACKGROUND OF THE INVENTION

This invention relates to a process, specifically to a process for preparing [1H]-isoindolin-1-one-3-carboxylic acid, a compound potentially useful as an intermediate leading to a surrogate for the amino acids proline or phenylglycine.

The literature procedure for preparing [1H]-Isoindolin-1-one-3-carboxylic acid consists of three individual reaction steps starting with the oxidation of naphthalene to phthalonic acid, followed by formation of 1-hydroxyphthalazin-4-carboxylic acid and its subsequent reduction to [1H]-Isoindolin-1-one-3-carboxylic acid. The literature procedure, J. Prakt. Chem., 146, 307 (1936), provides the product of the present process invention in an overall yield of 9-11%.

SUMMARY OF THE INVENTION

It has now been found that [1H]-Isoindolin-1-one-3-carboxylic acid can be prepared in 34% yield by a single vessel process which comprises the steps of (a) treating a solution of a compound of the formula

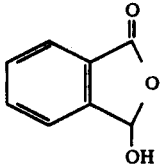

in an alkanol of one to three carbon atoms with ammonia, (b) contacting the resulting solution with an aqueous solution of an equimolar amount of an alkali metal cyanide, (c) removing the alkanol, (d) adjusting the pH to about 1.0, (e) heating the resulting reaction mixture until the formation of the product is substantially complete and isolating the product.

Preferred in the instant process is the use of methanol as the alkanol, sodium cyanide as the alkali metal cyanide and adjustment of the pH with hydrochloric acid.

DETAILED DESCRIPTION OF THE INVENTION

It is preferred that the initial step of the reaction be carried out in a reaction-inert solvent such as a $C_1$-$C_3$ alcohol. In practice, ammonia gas is bubbled into a cooled solution of phthaladehydic acid in said solvent until the solution is saturated.

Following the treatment with ammonia, the reaction mixture is treated with at least an equimolar amount of a cyanide in aqueous solution. In addition to any equimolar amount, an excess of 10% or greater can be added without changing the course of the reaction. Since it is preferred that said cyanide be freely soluble in water, alkali metal cyanides such as lithium, potassium and sodium cyanides are preferred.

After the cyanide has been added, the alkanol solvent is removed, preferably under vacuum at from room temperature to about 30° C. and the remaining aqueous solution treated with sufficient acid to provide a pH of about 1.0. Any acid strong enough to provide this pH can be employed. The preferred acid is hydrochloric in a concentration of about 6 N. During the initial addition period a precipitate forms and then redissolves.

The resulting acidic solution is heated for a period necessary to hydrolyze the cyano compound to an acid. A reaction period of 1.5-2 hours is usually sufficient at a temperature of 100° C.

The resulting solids which precipitate during hydrolysis are isolated by filtration or centrifugation.

The compound formed is identical to that reported by A. Darapsky, et al., J. Prakt. Chem., 146, 307 (1936).

As previously indicated the compound of the present invention is useful as an intermediate leading to octahydro-3-oxo-1H-isoindole-1-carboxylic acid, a reagent used in the synthesis of antihypertensive agents as taught in European patent application No. 58,567A.

The following example illustrates the invention.

EXAMPLE 1

[1H]-Isoindolin-1-one-3-carboxylic acid

Ammonia gas was bubbled into a cooled (10°-15° C.) solution of 10 g (0.0666 mole) of phthalaldehydic acid in 100 ml of methanol for 10 minutes, and the solution allowed to stir at room temperature for one hour. To the stirred solution was added a solution of 3.26 g (0.0666 mole) of sodium cyanide in 100 ml of water over a 15 minute period. After stirring at room temperature for one hour, most of the methanol was removed in vacuo and the resulting yellow solution was treated dropwise with 80 ml of 6 N hydrochloric acid over a 10 minute period, producing a transient precipitate followed by redissolution. The solution was heated at 100° C. for 1.5 hours, producing a thick yellow precipitate. The mixture was cooled to room temperature, the yellow solid filtered and washed with water and acetone. The resulting solid was recrystallized from water, 4.14 g (34% yield), m.p. 153°-154° C.

The product displayed physical properties in complete agreement with those described in the literature, Darapsky, et al., J. Prakt. Chem., 146, 307 (1936).

I claim:

1. A process for preparing a compound of the formula

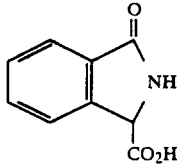

which comprises the steps of (a) treating a solution of a compound of the formula

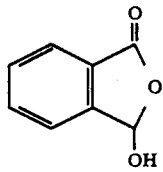

in an alkanol having one to three carbon atoms with ammonia, (b) contacting the resulting solution with an aqueous solution containing an equimolar amount of an alkali metal cyanide, (c) removing the alkanol, (d) adjusting the pH to about 1.0, (e) heating the resulting reaction mixture until the formation of the product is substantially complete and isolating the product.

2. The process of claim 1, wherein the alkanol is methanol, the alkali metal cyanide is sodium cyanide and adjusting the pH with hydrochloric acid.

* * * * *